(12) United States Patent
Satz

(10) Patent No.: US 11,357,874 B2
(45) Date of Patent: *Jun. 14, 2022

(54) TUMOR TARGETED RADIONUCLIDE THERAPY AND MOLECULAR IMAGING OF HER2+ CANCERS AND OTHER NEOPLASMS

(71) Applicant: Stanley Satz, Lake Worth, FL (US)

(72) Inventor: Stanley Satz, Lake Worth, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/568,236

(22) Filed: Sep. 11, 2019

(65) Prior Publication Data

US 2020/0085981 A1    Mar. 19, 2020

Related U.S. Application Data

(60) Provisional application No. 62/729,959, filed on Sep. 11, 2018.

(51) Int. Cl.
*A61K 51/10* (2006.01)
*G01N 33/574* (2006.01)
*A61K 51/08* (2006.01)
*C07K 16/22* (2006.01)

(52) U.S. Cl.
CPC ........ *A61K 51/1021* (2013.01); *A61K 51/088* (2013.01); *A61K 51/1027* (2013.01); *A61K 51/1096* (2013.01); *C07K 16/22* (2013.01); *G01N 33/574* (2013.01); *A61K 2123/00* (2013.01); *C07K 2317/77* (2013.01)

(58) Field of Classification Search
CPC ...... A61K 51/00; A61K 51/08; A61K 51/083; A61K 51/088; A61K 51/1021; A61K 51/1096; A61K 51/0497; A61K 51/0459; A61K 2123/00; A61K 2121/00; A61K 51/1027; C07K 16/22; C07K 16/2818; C07K 2317/77; G01N 33/574
USPC .......... 424/1.11, 1.49, 1.65, 1.69, 1.81, 1.85, 424/1.89, 9.1, 9.2, 9.3, 9.4, 9.5, 9.6; 514/1, 1.1, 19.2, 19.3, 19.4, 19.5, 19.6; 530/300; 534/7, 10–16

See application file for complete search history.

(56) References Cited

U.S. PATENT DOCUMENTS

| | | | |
|---|---|---|---|
| 5,804,157 | A | 9/1998 | Srinivasan et al. |
| 5,830,431 | A | 11/1998 | Srinivasan et al. |
| 7,300,940 | B2 | 11/2007 | Danthi et al. |
| 7,858,803 | B2 | 12/2010 | Elmaleh et al. |
| 9,586,916 | B2 | 3/2017 | Goodnow, Jr. et al. |
| 2011/0236307 | A1 | 9/2011 | Jones |
| 2014/0044646 | A1 | 2/2014 | Li et al. |
| 2015/0038523 | A1 | 2/2015 | Goodnow, Jr. |
| 2015/0175553 | A1 | 6/2015 | Wouters et al. |
| 2016/0375157 | A1 | 12/2016 | Azhdarinia et al. |
| 2017/0173161 | A1 | 6/2017 | Kaplan et al. |

FOREIGN PATENT DOCUMENTS

| | | |
|---|---|---|
| WO | 2006133732 A1 | 12/2006 |
| WO | 2016000798 A1 | 1/2013 |
| WO | 2013079578 A1 | 6/2013 |
| WO | 2014029016 A1 | 2/2014 |
| WO | 2015055806 A1 | 4/2015 |

OTHER PUBLICATIONS

Baum et al, Cancer Biotherapy and Radiopharmaceutical, vol. 30, No. 4, pp. 152-159 (Year: 2015).*
Westerlund et al, Mol. Pharmaceutics, vol. 13, pp. 1668-1678 (Year: 2016).*
Dolan et al, Cancer Control, vol. 21, No. 3, pp. 231-237 (Year: 2014).*
Weineisen et al, EJNMMI Research, No. 63, pp. 1-15 (Year: 2014).*
Yeong et al, Biomed. & Biotechnol., vol. 15, No. 10, pp. 845-863 (Year: 2014).*
Yan et al, Cancer Metastasis Rev, vol. 34, pp. 157-164 (Year: 2015).*
Kim et al, Bioorganic & Medicinal Chemistry Letters, vol. 22, pp. 5517-5522 (Year: 2012).*
Baum et al., "First-In-Human Study Demonstrating Tumor-Angiogensis by PET/CT Imaging with 68Ga-NODAGA-Theranost, a High-Affinity Peptidomimetic for alphavbeta3 Integrin Receptor Targeting" Cancer Biotherapy and Radiopharmaceuticals. May 1, 2015 (May 1, 2015) vol. 1, pp. 152-159.
Klara Soukup et al., "Radiation meets immunotherapy—a perfect match in the era of combination therapy?", International Journal of Radiation Biology., vol. 91, No. 4, Feb. 9, 2015 (Feb. 9, 2015), pp. 299-305, XP055320015, ISSN: 0955-3002, DOI: 10.3109/09553002.2014.995383.
Gregory K Pennock et al., "The Evolving Role of Immune Checkpoint Inhibitors in Cancer Treatment", The Oncologist, Jun. 11, 2015 (Jun. 11, 2015), pp. 812-822, XP055320470, Retrieved from the InterHer2+ <URL: http://theoncologist.alphamedpress.org/content/20/7/812.full.pdf#page=1&view=FitH> [retrieved on Nov. 17, 2016], DOI: 10.1634/theoncologist.2014.

(Continued)

*Primary Examiner* — Michael G. Hartley
(74) *Attorney, Agent, or Firm* — Bonini IP Law, LLC; Frank J. Bonini, Jr.

(57) ABSTRACT

Methods and compositions for treating, diagnosing and staging cancers, in particular overexpressing the Human Epidermal growth factor Receptor 2 protein (HER2+) given rise to in breast, gastric, gastroesophageal, ovarian, pancreatic cancer and brain tumors, which may be metastatic to the brain or other site. More specifically, the invention provides for Targeted Radionuclide Therapy (TRNT) with a compound of the invention having a peptide that targets the HER2+ cells, a second component for combining metals into complexes through a ring structure (DOTA), and a third radioisotope component, Lu-177 and Ga-68, in which embodiments further include a companion diagnostic, and in which embodiments further include anti-integrin precision medicines for cancers expressing $\alpha v \beta 3$ and $\alpha v \beta 5$ integrins, HER2+, vascular endothelial growth factor, vitronectin, fibronectin, tenascin, reelin, kindlin and talin. TRNT may be administered alone or in combination with standard-of-care; an immunooncologic and/or chemotherapeutic, adjuvantly or neoadjuvantly.

10 Claims, No Drawings

(56) References Cited

OTHER PUBLICATIONS

Imhof et al., "Response, Survival, and Long-Term Toxicity After Therapy With the Radiolabeled Somatostatin Analogue [90Y-DOTA]-TOC in Metastasized HER2+ Cancers", J. Clin . Oncol, vol. 29, 2011, pp. 2416-231.
Wynick D., et al., "Resistance of metastatic pancreatic endocrine tumors after longterm treatment with the somatostatin analogue octreotide (SMS 201-995)." Clin. Endocrinol. 30(4), 385-388 (1989).
Linnenbacher, M., and Maletzki, C., "Tumor-infiltrating B cells: The ignored players in tumor immunology." Oncoimmunology. Oct. 1, 2012 ;1 (7):1 186-1 188.
Q.-T. Le. et al: "Emerging Treatment Paradigms in Radiation Oncology", Clinical Cancer Research, vol. 21, No. 15, May 19, 2015 (May 19, 2015), US, pp. 3393-3401, XP055320682, ISSN: 1078-0432, DOI: 10.1158/1078-0432.CCR-14-1191.
Kwon ED, Drake CG, Scher, H I, Fizazi, K, Bossi, A., Van Den Eertwegh, A.J., et al., "Ipilimumab versus placebo after radiotherapy in patients with metastatic castration-resistant prostate cancer that had progressed after docetaxel chemotherapy (CA184-043): a multicentre, randomised, doubleblind, phase 3 trial" Lancet Oncol Jun. 2014;15:700-12.
Slovin SF, Higano CS, Hamid O, Tejwani S, Harzstark A, Alumkal JJ, et al. Ipilimumab alone or in combination with radiotherapy in metastatic castration-resistant prostate cancer: results from an open-label, multicenter phase I/II study. Ann Oncol 2013;24:1813-21.
Maribel L Sierra et al: "Lymphocytic Toxicity in Patients After Peptide-Receptor Radionuclide Therapy (TRNT) with 177 Lu-DOTATATE and 90 Y-DOTATOC", Dec. 1, 2009 (Dec. 1, 2009), XP055319785, Retrieved from the Interher <URL:http://online.liebertpub.com/doi/pdf/10.1089/cbr.2009.0641> [retrieved on Nov. 15, 2016].
Ricci S: "Long-acting depot lanreotide in the treatment of patients with advanced HER2+ tumors", Am. J. Clin. Oncol., vol. 23, No. 4, 2000, pp. 412-415.
Peggs KS, Quezada SA, Chambers CA, et al. "Blockade of CTLA-4 on both effector and regulatory T cell compartments contributes to the antitumor activity of anti-CTLA-4 antibodies." J. Exp. Med. 2009; vol. 206:1717-25.
Krummel MF, Allison JP. CTLA-4 engagement inhibits IL-2 accumulation and cell cycle progression upon activation of resting T cells. J Exp Med. 1996;183:2533-40.
Ralph E. Vatner et al: "Combinations of immunotherapy and radiation in cancer therapy", Frontiers in Oncology, vol. 4, Nov. 28, 2014 (Nov. 28, 2014), pp. 1-15, XP055320019, DOI: 10.3389/fonc.2014.00325.
S. C. Formenti et al: "Combining Radiotherapy and Cancer Immunotherapy: A Paradigm Shift", Journal of the National Cancer Institute, vol. 105, No. 4, Jan. 4, 2013 (Jan. 4, 2013), GB, pp. 256-265, XP055319703, ISSN: 0027-8874, DOI: 10.1093/jnci/djs629.
Nelson BH, "CD20B cells: the other tumor-infiltrating lymphocytes." J. Immunol. Nov. 1, 2010 ;185(9):4977-82.
Grimaldi, Antonio M, et al., "Abscopal effects of radiotherapy on advanced melanoma patients who progressed after ipilimumab immunotherapy", OncoImmunology, vol. 3, e28780-9; May 2014; Landes Bioscience.
Schultheis, Anne M. et al., "PD-L1 expression in small cell neuroendocrine carcinomas", European Journal of Cancer (2015) 51, 421-426.
Antonia SJ, Goldberg S, Balmanoukian AS, et al. Phase Ib study of MEDI4736, a programmed cell death ligand-1 (PD-L1) antibody, in combination with tremelimumab, a cytotoxic T-lymphocyte-associated protein-4 (CTLA-4) antibody, in patients (pts) with advanced NSCLC. J Clin Oncol. 2015;33(suppl; abstr3014).
Kaur, Balveen et al.; "Hypoxia and the hypoxia-inducible-factor pathway in glioma growth and angiogenesis" Society for Neuro-Oncology; Apr. 2005, pp. 134-153 (2005).

Antonia SJ, Gettinger SN, Chow LQM, et al., "Nivolumab and ipilimumab in first-line NSCLC: interim phase I results" J. Clin. Oncol. 2014;32(5s suppl; abstr 8023).
Pardoll D M, "The blockade of immune checkpoints in cancer immunotherapy", Nat Rev Cancer. 2012;12(4):252-264.
Sharma P, Wagner K, Wolchok JD, Allison JP, "Novel cancer immunotherapy agents with survival benefit: recent successes and next steps", Nat Rev Cancer. 2011; 11(11):805-812 (2011).
Phan AT, Oberg K, Choi J, Harrison LH JR, Hassan MM, StTrosberg JR, Krenning EP, Kocha W, Woltering EA, Maples WJ; North American HER2+ Tumor Society (NAHER2+ S). NAHER2+ S consensus guideline for the diagnosis and management of HER2+ tumors: well-differentiated HER2+ tumors of the thorax (includes lung and thymus), Pancreas. Aug. 2010;39(6):784-98.
Bodei L; Kidd M et al.: "Long-term tolerability of TRNT in 807 patients with HER2+ tumors: the value and limitations of clinical factors", Eur J Nucl Med Mol Imaging, 2014.
Simpson TR, Li F, Montalvo-Ortiz W, et al., "Fc-dependent depletion of tumor-infiltrating regulatory T cells co-defines the efficacy of anti-CTLA-4", Journal of Experimental Medicine, 2013 vol. 210 No. 9, 1695-1710.
Krummel MF, Allison JP, "CD28 and CTLA-4 have opposing effects on the response of T cells to stimulation", J Exp Med. 1995;182:459-65.
Linsley PS, Brady W, Urnes M, et al., "CTLA-4 is a second receptor for the B cell activation antigen B7", J Exp Med. 1991 ;174:561-9.
Denoyer D; Lobachevsky P; Jackson P; Thompson M; Martin OA; Hicks RJ: "Analysis of 177Lu-DOTA-octreotate therapy-induced DNA damage in peripheral blood lymphocytes of patients with HER2+ tumors", J Nucl Med, vol. 56, No. 4, Apr. 2015 (Apr. 1, 2015), pp. 505-511.
Baum Richard P et al: "Molecular Imaging of HER2-Expressing Malignant Tumors in Breast Cancer Patients Using Synthetic 111In- or 68Ga-Labeled Affibody Molecules", The Journal of Nuclear Medicine, May 19, 2010, DOI: 10.2967/jnumed.109.073239.
Wu Y et al., "Induction of Anti-Tumor Immune Responses by Peptide Receptor Radionuclide Therapy with 177Lu-DOTATATE in a Murine Model of a Human Neuroendocrine Tumor Diagnostics", 3, 344-355, 2013.
Wing K, Onishi Y, Prieto-Martin P, et al., "CTLA-4 control over Foxp3regulatory T cell function," Science. 2008; 322:271-5.
Wynick D., "The use of the long-acting somatostatin analog octreotide in the treatment of gut HER2+ tumors", J. Clin. Endocrinol. Metab. 73(1), 1-3 (1991).
Bernstein M. et al., "Radiation-Induced Modulation of Costimulatory and Coinhibitory T-Cell Signaling Molecules on Human Prostate Carcinoma Cells Promotes Productive Antitumor Immune Interactions," Cancer Biotherapy and Radiopharmaceuticals, 29(4): 153161, 2014.
Johannes Schwazenberg, et al., "Treatment Response Evaluation using 18F-FDOPA PET in Patients with Recurrent Malignant Glioma on Bevacizumab Therapy", Clin. Cancer Res. Author manuscript; available in PMC Jul. 1, 2015.
Magdy Khalil, "Basic Science of PET Imaging", Nov. 2016, preface and contents listing.
Aigbirhio et al., "Efficient regioselective labelling of the CFC alternative 1,1,1,2-tetrafluoroethane (HFC-134a) with fluorine-18", J Fluor Chem, vol. 70, 1995, pp. 279-287.
Greene; Wuts: "Protective Groups in Organic Synthesis", 2007, John Wiley & SONS, summary in JACS book Yeviews, J. Am. Chem. Soc. 2007, 129, 1009-1012.
G.H. Strejan, J.J. Gilbert and J. St. Louis, "Suppression of Chronic-Relapsing Experimental Allergic Encephalomyelitis in Strain-13 Guinea Pigs by Administration of Liposome-Associated Myelin Basic Protein" J. Neuroimmunol. 1984, 7, pp. 27-41.
Stephen M. Berge, et al., "Pharmaceutical Salts", J. Pharm. Sci. 1977, 66, pp. 1-19.
Marchand Patrice, Ouadi Ali, Pellicioli Michel, Schuler Jacky, Laquerriere Patrice, Boisson Fr'ed'eric, Brasse David, "Automated and efficient radio synthesis of [18F] FLT using a low amount of precursor," Nuclear Medicine and Biology 43 (2016), pp. 520-527.
Periodic Table of the Elements, CAS version, "Handbook of Chemistry and Physics", 67th Ed., 1986-1987.

(56) References Cited

OTHER PUBLICATIONS

Welch; Redvanly: "Handbook of Radiopharmaceuticals", 2003, Wiley, Chapters 6 and 8, pp. 195-227, and 283-306.
American Cancer Society. "Cancer Facts & Figures 2014", Atlanta: American Cancer Society; 2014.
Masaki, Y. et al., "The accumulation mechanism of the hypoxia imaging probe "FMISO" by imaging mass spectrometry: possible involvement of low-molecular metabolites." Sci. Rep. 5, 16802; doi: 10.1038/srep16802 (2015).
Ramodiga, et al., ChemComm., 2013, 49, 4270-4739.

* cited by examiner

TUMOR TARGETED RADIONUCLIDE THERAPY AND MOLECULAR IMAGING OF HER2+ CANCERS AND OTHER NEOPLASMS

CROSS-REFERENCE TO RELATED APPLICATION

This application claims the benefit of priority to U.S. Provisional Application Ser. No. 62/729,959, filed on Sep. 11, 2018, the complete contents of which are herein incorporated by reference.

BACKGROUND OF THE INVENTION

1. Field of the Invention

The present invention relates to the field of cancer diagnosis and therapy, and more particularly to treating, diagnosing and staging cancers, and, in particular, to cancers overexpressing the Human Epidermal growth factor Receptor 2 protein (HER2+), and the use of compounds to treat, diagnose and stage cancers.

2. Brief Description of the Related Art

Breast cancer is the most common cancer in women worldwide, with nearly 1.7 million new cases diagnosed in 2017, representing about 25 percent of all cancers in women. HER2+breast cancer is a type of cancer that tests positive for a protein called human epidermal growth factor receptor 2 (HER2+), which promotes the growth of cancer cells. In about 1 of every 5 breast cancers, the cancer cells have a gene mutation that makes an excess of the HER2+ protein. HER2+breast cancers tend to be more aggressive than other types of breast cancer. They are less likely to be sensitive to hormone therapy, though many people with HER2+breast cancer can still benefit from hormone therapy. Treatments that specifically target HER2+ are very effective. In marked contrast, these treatments are so effective that the prognosis for HER2+breast cancer is actually quite good. However, HER2+ cancer is not limited to the breast.

The widely used chemotherapy drug trastuzumab (Herceptin), a standard-of-care, can be life-saving for women with HER2-positive breast cancer, a particularly aggressive form of the disease. But new research now adds to mounting evidence that the treatment can take a toll on the heart, increasing the risk for heart failure. In many cases, the benefits of the chemotherapy still outweigh the risks. Cardiotoxicity in younger women and the risk of heart failure increased with age. Taking other chemotherapy drugs, known as anthracyclines, could also increase the likelihood of heart problems. Comorbidities such as diabetes, which tend to be associated with obesity, were associated with a higher risk of heart failure. Breast cancer patients treated with Herceptin require regular heart monitoring. Heart disease has been considered and reported to be the second leading cause of death among breast cancer survivors mainly due to the toxic effects of some cancer treatments. This underscores the need for novel adjuvant or neoadjuvant therapy to treat both early and late stage HER2+ cancers, alone or together with standard of care, i.e., the focus of this patent.

HER2+

Receptor tyrosine-protein kinase erbB-2, also known as CD340, proto-oncogene Neu, Erbb2, or ERBB2, is a protein that in humans is encoded by the ERBB2 gene. It is frequently called HER2+ or HER2+/neu. HER2+ neoplasia occurs in a variety of organ sites and tissue types including breast, gastric, gastroesophageal junction adenocarcinoma, and pancreas. HER2+ tumors have a range of morphologic, functional, and behavioral characteristics. Moreover, in addition to the breast, this cancer has the potential to spread to other organs such as the brain, and when they do, they can be especially life threatening and difficult to treat with current modalities. Heterogeneous tumors originating from HER2+ proteins typically begin in the breast but may be distributed throughout the body.

Some patients have breast tumors, gastric or gastroesophageal junction tumors that contain cancers with higher levels of a protein known as HER2/neu, which is a growth-promoting protein on the outside of breast cancer cells with higher than normal levels of HER2 are called HER2-positive (HER2+). These cancers tend to grow and spread faster than other breast cancers. A biopsy or surgery sample of the cancer is usually tested with either immunohistochemical stains (IHC) or Fluorescent in situ hybridization (FISH). Many breast cancer specialists think that the FISH test is more accurate than IHC. However, it is more expensive and takes longer to get the results. Often the IHC test is done first. If the result is 0 or 1+, the cancer is considered HER2-negative. They do not respond to treatment with drugs that target HER2. If the result is 3+, the cancer is HER2-positive. They are usually treated with drugs that target HER2. If the result is 2+, the HER2 status of the tumor is not clear and is called "equivocal." This means that the HER2 status needs to be tested with FISH to clarify the result. Triple-negative breast tumors do not have much HER2 and also don't have estrogen or progesterone receptors. They are HER2-, ER-, and PR-negative. These cancers are more common in younger women and in African-American or Hispanic/Latina women. Triple-negative breast cancers grow and spread more quickly than most other types of breast cancer. Because the cancer cells don't have hormone receptors, hormone therapy is not helpful in treating these cancers. Because they do not have too much HER2, drugs that target HER2 are not helpful, either. Chemotherapy can still be useful, though. Triple-positive breast tumors are HER2-, ER-, and PR-positive. These cancers are treated with hormone drugs as well as drugs that target HER2.

Normally, HER2+ receptors help control how a healthy breast cell grows, divides, and repairs itself. But in about 25% of breast cancers, the HER2+ gene doesn't work correctly and makes too many copies of itself (known as HER2+ gene amplification). All these extra HER2+ genes tell breast cells to make too many HER2+ receptors (HER2+ protein overexpression). This makes breast cells grow and divide in an uncontrolled way.

Breast cancers with HER2+ gene amplification or HER2+ protein overexpression are called HER2+ in the pathology report. HER2+breast cancers tend to grow faster and are more likely to spread and come back compared to HER2+-negative breast cancers. But there are medicines specifically for HER2+breast cancers.

The HER2+ protein can cause normal cells to grow uncontrollably like aggressive cancer cells. If HER2+ is blocked, the growth of HER2+breast and other cancers might be slowed. The HER2+ protein can cause normal cells to grow uncontrollably like aggressive cancer cells. If HER2+ is blocked, the growth of HER2+breast and other cancers might be slowed. The gene for HER2+ is located on chromosome 17 and has been found to be amplified with an increased copy number in several cancers (Jorgensen 2010). Amplification of HER2+ has been found to promote tumorigenesis and to be involved in the pathogenesis of several human cancers (Moasser 2007).

It also has been reported that breast cancer in patients treated with an immunotherapeutic, trastuzumab and chemotherapy grew at a slower rate than in patients treated with chemotherapy alone; and that subsequent clinical trials also showed positive outcomes among women with early-stage HER2+breast cancer. Despite successes with trastuzumab, pertuzumab, other immunotherapies and chemotherapies such as docetaxel, many women with breast cancer do not benefit from current HER2+-targeted treatments, or they become resistant to the effects of these drugs after initial treatment. Therefore, researchers continue to test new or modified drug combinations. The FDA approved pertuzumab as a treatment for women with HER2+metastatic breast cancer to be used in combination with trastuzumab and docetaxel, a chemotherapy drug. Other drugs that have been approved for the treatment of HER2+breast cancer include ado-trastuzumab emtansine, lapatinib ditosylate, and neratinib maleate. In 2017, pertuzumab received approval for use in combination with the same drugs as an adjuvant treatment for patients with HER2+ early breast cancer at high risk of recurrence. Nevertheless, the use of chemotherapy and immunotherapy has side effects including nausea, vomiting, hair loss, bone pain, peripheral neuropathy, skin rashes and because of toxicity, a very high incidence of cardiovascular disease. Nevertheless, there still is a high rate of cancer relapse and metastases.

Although tumors produce certain proteins, hormones and other chemicals that often cause patients to exhibit symptoms, the non-specific nature of these symptoms can lead to delayed diagnosis or even a misdiagnosis. By the time patients are correctly diagnosed, the cancer has usually metastasized, with regional or distant metastasis observed in approximately 30% of cases. Once they have metastasized, HER2+ tumors may not be effectively treated by surgery alone and generally are not curable. Despite the major advance in the therapy of HER2+breast cancer represented by treatment protocols containing trastuzumab, a first line treatment, nearly all patients given trastuzumab for advanced breast cancer will ultimately experience progression, while a significant proportion of patients receiving this treatment in the setting of early breast cancer will experience disease recurrence. Some may receive trastuzumab in the metastatic setting, but again, will likely experience progression despite this treatment (Murphy 2012).

While breast cancer is the most common cancer among women in the United States, not all breast cancers are the same. There are ten different types of breast cancer, which are determined by the specific cells in the breast that are affected, according to the American Cancer Society. HER2+ breast cancer accounts for around 20 percent of breast cancer. It is also associated with an increased recurrence risk and poor five-year survival rates relative to other breast cancers. A woman faced with breast cancer, of course, hopes for a definitive test that can tell her what form of cancer she has, and the best steps to treat it. Presently, genetic testing for breast cancer looks mostly at the genetic changes that come from a person's parents and grandparents, and the increased risk of being genetically predisposed to some cancers. Only 5 to 10 percent of breast cancers are inherited genetically, according to the American Cancer Society. HER2+breast cancer is a difficult breast cancer to treat because screening tests do not often "catch it" before it becomes serious and the usual drugs that target estrogen, progesterone, and HER-2 may be ineffective. Trastuzumab (Herceptin) has become the standard of care for treatment of eligible women with stage II and III HER2+breast cancer, and it is frequently considered for stage I breast cancer as well.

Studies have been performed using diagnostic testing on women with HER2+breast cancer. Twenty one cancer genes make breast cancer more likely. The proteins or genes, when altered, that increased the risk of triple-negative breast cancer in the women included those that are involved, there's a greater than 20 percent lifetime risk for all types of breast cancer. One study establishes which genes are associated with high risks of HER2+breast cancer, and the findings show this and identify new specific and strong associations between the susceptibility genes and HER2+ breast cancer risk.

Immunotherapy Collateral Effects

While immunotherapeutics such as Trastuzumab have become a part of the standard-of-care armamentarium for HER2+ cancers, the following are common (occurring in greater than 30%) side effects in patients taking Trastuzumab and/or Avastin for treatment of HER2+ cancer: nausea, vomiting, cardiovascular disease, generalized weakness, muscle aches, pain, unusually weak or tired, poor appetite, constipation, breathing difficulties, chest pain or palpitations, cough, dizziness or fainting, fever or chills, sore throat, skin rash, itching or hives, upper respiratory infection, cough, low white blood cell count and increased risk for infection, proteinuria (kidney problems), nose bleed (bleeding problems), diarrhea, hair loss, mouth sores, headache, swelling of the legs or ankles, impaired fertility by several effects. Some patients do not recover completely or recover very slowly following discontinuation of the drug. Targeted radionuclide therapy (TRNT) does not result in these collateral effects. Salivary gland toxicity can occur in some patients receiving TENT and is treated with Botox. Potential kidney toxicity is ameliorated or treated with an amino acid blocker.

Moreover, increased angiogenesis is a marker of aggressiveness in many cancers. Targeted radionuclide therapy of these cancers with angiogenesis-targeting agents may curtail this increased blood vessel formation and slow the growth of tumors, both primary and metastatic.

Therefore, there is a significant need for therapies for HER2+ tumors, however, there are only a limited number of options currently available for the treatment.

The cornerstone for treatment of HER2+ tumors is the use of Trastuzumab and chemotherapy in the neoadjuvant setting. Chemotherapy and targeted therapies have been registered for many cancers while for HER2+ brain metastases only have a limited approval of use. As a result of that, many patients exhaust all the available treatment options, particularly in the advanced disease setting, which represents a high unmet medical need for systemic treatments of metastatic HER2+ tumors.

At a symptomatic level, integrins are used to control certain clinical syndromes with HER2+ positive tumors.

Most HER2+ tumors overexpress HER2 positive protein receptors. These protein receptors are expressed in human cells that sense molecules outside of the cell and activate sub-cellular events in response to integrin treatments.

However, the symptomatic targeting of theranostics is distinct from treating the metastatic HER2+ cancerous cells and tumors themselves. Trastuzumab is a HER2+/neu receptor antagonist indicated for the treatment of HER2+ overexpressing breast cancer and the treatment of HER2+- overexpressing metastatic gastric or gastroesophageal junction adenocarcinoma. Based on a partial antiproliferative effect. Trastuzumab, a humanized monoclonal antibody inhibiting vascular endothelial growth factor was approved by the FDA for the treatment of patients with well-differentiated or moderately-differentiated, locally advanced or metastatic HER2+ tumors. has been approved in the US for treatment of HER2 cancers.

These are "antitumoral" therapy so far approved for HER2+ tumors. However, when the tumor becomes resistant or unresponsive to its effects, usually several months after the initiation of treatment, there are no other approved therapies for intervention. These tumors therefore are unbeatable by the currently available therapies.

While chemotherapeutic agents and surgery and some targeted therapies have become the standard of care for HER2+ tumors, the response rates vary according to tumor aggressiveness but are estimated to be between approximately 30% and 50% for targeted therapies (RT) have been approved for the treatment of HER2+ tumors with limited survival benefit.

Thus, traditional chemotherapy has little place in treatment of HER2+ tumors, since most of these tumors are difficult to treat. A rigorous assessment of the efficacy of chemotherapy in literature is hampered by the prevalence of retrospective studies on heterogeneous series of patients, where toxicity is relevant, and the responses are short-lived and sporadic. Many schemes, including single or multiple agents, have been attempted.

SUMMARY OF THE INVENTION

The present invention relates to methods of treating a patient affected by a tumor that over-expresses receptors comprising administering to said patient a combination of a TRNT and imaging of HER2+ cancers.

This invention concerns peptidomimetic compounds as highly potent and selective antagonists of the αvβ3 and αvβ5 integrin receptor which may contain the Arg-Gly-Asp sequence for diagnosis and tumor targeted radionuclide therapy (TRNT) and molecular imaging. The compounds of the invention may be used as a novel class of anticancer drugs and/or diagnostic tracers as suitable tools for TRNT and imaging of HER2+ cancers. Embodiments of the present invention provide a combination therapy approach that for many, could effectively treat HER2+ tumors. Therapeutic compositions of the invention comprise peptidomimetic compounds that are radiolabeled that are employed for use in conjunction with a pharmaceutically acceptable excipient for delivery to a patient to treat a cancer, and more particularly a cancer that has a human epidermal growth factor receptor 2-Positive (hereinafter referred to as HER2+), or other cancer that overexpress integrin receptors. The compositions are used by delivering dosages of the composition to a patient, preferably intravenously, and over the course of time (the treatment term). The patent is monitored using imaging to determine the effectiveness of the treatment. Use of imaging compositions of the invention also is disclosed, wherein these diagnostic compositions are paired with the therapeutic composition.

According to preferred embodiments, the method is carried out to deliver a targeted radionuclide therapy (TRNT). According to preferred implementations, the method involves the TRNT by administration to a patient of an effective amount of a radioligand, and more preferably a radioligand comprised of an anti-integrin peptidomimetic, a chelator, and a radionuclide. The administration of the radioligand to a patient may include administration of a radioligand where the radionuclide is $^{177}$Lu or [225] Actinium. In specific embodiments, the TRNT is [177] Lutetium the integrin peptidomimetic, and more particularly, Lu-177 DOTAGA IAC: A ligand containing the active moiety, the αVβ3 integrin antagonist peptidomimetic, 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) and 1-(1-carboxy-3-carbotertbutoxymethyl)-1,4,7,10-tetraazacyclododecane (DOTAGA) (tBu)$_4$ and radiolabeled with Lutetium-177 for tumor targeted radionuclide therapy.

In the preferred embodiments, the 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) is conjugated to the 1-(1-carboxy-3-carbotertbutoxymethyl)-1,4,7,10-tetraazacyclododecane (DOTAGA) (tBu)$_4$, and radiolabeled.

According to embodiments, the radionuclide may comprise one or more of the following: Lutetium-177, Actinium-225, Bismuth-213, Thorium-227, Lead-212, Astatine-211, Yttrium-90, Iodine-131, Gallium-68, Zirconium-68, or other therapeutic radiolabel.

The present invention relates to methods of treating, diagnosing and staging cancers, in particular overexpressing the Human Epidermal growth factor Receptor 2 protein (HER2+) given rise to in breast, gastric, gastroesophageal, ovarian and pancreatic cancer, and which may be metastatic to the brain or other site. More specifically, the invention provides for Targeted Radionuclide Therapy (TRNT) with the radiolabeled composition of the invention and a companion diagnostic, (such as, for example, Ga-68 labeled ligand, Ga-68-NODAGA IAC), anti-integrin precision medicines for cancers expressing αvβ3 and αvβ5 integrins, HER2+, vascular endothelial growth factor, vitronectin, fibronectin, tenascin, reelin, kindlin and talin. TRNT may be administered alone or in combination with standard-of-care; an immunooncologic and/or chemotherapeutic, adjuvantly or neoadjuvantly.

A preferred diagnostic composition, which may serve as the companion diagnostic, may comprise Ga-68-NODAGA IAC: A ligand containing the active moiety, the αVβ3 integrin antagonist peptidomimetic 4-[2-(3,4,5,6-tetrahydropyrimidine-2-ylamino)ethyloxy]benzoyl-2-[N-(3-aminoneopenta-1-carbamyl)]-aminoethylsulfonyl-amino-β-alanine (IAC) and 1-(1-carboxy-3-carbo-t-butoxypropyl)-4,7-(carbo-tert-butoxymethyl)-1,4,7-triazacyclononane, and radiolabeled with [68]Ga. The diagnostic may be administered to the patient, and the appropriate imaging study or studies carried out to determine the location and density of the marker.

The 4-[2-(3,4,5,6-tetrahydropyrimidine-2-ylamino)ethyloxy]benzoyl-2-[N-(3-aminoneopenta-1-carbamyl)]-aminoethylsulfonyl-amino-β-alanine (IAC) preferably is conjugated to 1-(1-carboxy-3-carbo-t-butoxypropyl)-4,7-(carbo-tert-butoxymethyl)-1,4,7-triazacyclononane, and labeled with a radionuclide.

Preferred embodiments of the method involve the use of an αvβ3/αvβ5 anti-integrin antagonist peptidomimetic for the diagnosis and treatment of cancers comprising administering to a patient a pharmaceutical composition. According to preferred embodiments, the composition includes a therapeutically effective amount of the αvβ3 and αvβ5 antagonist peptidomimetic compound, covalently linked by a spacer sequence wherein the compound may be a linear artificial sequence, a chelator such as NODAGA, DOTAGA, DOTATATE, or CHX-A, and a pharmaceutically acceptable excipient for tumor targeted radionuclide therapy. The radionuclide is attached to the composition, preferably, via the chelator. For example, a peptidomimetic may be synthesized by any suitable production method, including for example, one such exemplary method which comprises a solid-phase method using Fmoc chemistry (e.g., amino acids are coupled according to the HBTU/HOBt/DIPEA procedure (Fields, C. G.; et al Pept. Res. 1991, 4, 95-101); and where final deprotection and cleavage form the resin are achieved with TFA and scavengers; and where purity and the identity of the peptides may be confirmed by analytical RP-HPLC and MALDI-TOF mass spectrometry. Peptidomimetics also may be synthesized on an automated peptide synthesizer using Fmoc solid-phase strategy (0.25 mmol).

The method involves administering compounds that contain $\alpha v\beta 3$ and $\alpha v\beta 5$ anti-integrin antagonist peptidomimetic, which, unlike cyclical peptides, display highly selective affinity for the HER2+ protein, vascular endothelia growth factor vitronectin, fibronectin, tenascin, reelin, kindlin, talin or combinations thereof for the diagnosis or prognosis of disorders using PET, SPECT and MRI by administering an effective amount of $\alpha v\beta 3/\alpha v\beta 5$ anti-integrin antagonist peptidomimetic thereof to a subject, particularly for the diagnosis of diseases related to metastasis and angiogenesis such as breast cancer, lung cancer, ovarian cancer, gastric cancer, esophageal cancer, blood borne cancers, musculoskeletal tumors, melanoma, head and neck cancer, human glioma, vascular restenosis, osteoporosis, rheumatoid arthritis.

The method may also include providing a diagnostic kit or synthesizer cartridges and administering the pharmaceutical treatment and/or diagnostic composition once the composition has been synthesized or generated from the kit. For example, diagnostic kits or synthesizer cartridges comprising the $\alpha v\beta 3$ and $\alpha v\beta 5$ peptidomimetic antagonist attached to a chelator such as NODAGA, DOTAGA, DOTATATE, or CHX-A or a nanocarrier such as a gold nanoparticle for the early detection, which may be in tissue, bone or in plasma for treatment of pathologies, such as breast cancer, esophageal cancer, lung cancers, ovarian cancer, gastric cancer, musculoskeletal tumors, melanoma, head and neck cancer, human glioma, cervical cancer, vascular restenosis, osteoporosis, rheumatoid arthritis.

In specific embodiments, the Immuno-Oncology (1-0) therapy comprises administering an inhibitor that inhibits the PD-1/PD-L 1 and CTLA-4 pathway. In other embodiments, the inhibitors of the PD-1/PD-L 1 and CTLA-4 pathway are antibodies that target the PD-1/PD-L 1 axis or the CTLA-4/B7 receptor complex. In still further HER2+ embodiments, the inhibitor of the PD-1/PD-L 1 pathway is a combination of inhibitors that target both PD-1 and PD-L 1.

In particular embodiments, the PD-1/PD-L1 or CTLA-4/B7 pathway inhibitors are selected from the group consisting of Nivolumab, MK-3475, MPDL3280A, MED14736, ipilimumab, and tremelimumab.

The invention is particularly defined by embodiments in which the cancer is a HER2+ tumor. More specifically, said treating comprises one or more of inhibiting the growth of a HER2+ tumor, inhibiting proliferation of HER2+ tumor cells, inhibiting HER2+ tumor metastases, reducing tumorigenicity of HER2+ tumor cells and methods of reducing the frequency of cancer stem cells or tumor initiating cells in a HER2+ tumor.

Any HER2+ tumor that expresses or overexpressed somatostatin receptors may be treated by the methods of the present invention. Exemplary such tumors include but are not limited to the group consisting of a gastroenteropancreatic HER2+ tumor, carcinoid tumor, pheochromocytoma, paraganglioma, medullary thyroid cancer, pulmonary HER2+ tumor, thymic HER2+ tumor, carcinoid tumor or pancreatic HER2+ tumor, pituitary adenoma, adrenal gland tumors, Merkel cell carcinoma, breast cancer, Non-Hodgkins lymphoma, Hodgkin lymphoma, Head & Neck tumor, urothelial carcinoma (bladder), Renal Cell Carcinoma, Hepatocellular Carcinoma, GIST, neuroblastoma, bile duct tumor, cervix tumor, Ewing sarcoma, osteosarcoma, small cell and non small cell lung cancer, prostate cancer, melanoma, meningioma, glioma, medulloblastoma hemangioblastoma, supratentorial primitive, neuroectodermal tumor, and esthesioneuroblastoma.

The HER2+ tumor is selected from the group consisting of functional carcinoid tumor, insulinoma, gastrinoma, vaso active intestinal peptide (VIP) oma, glucagonoma, serotoninoma, histaminoma, ACTHoma, pheochromocytoma, and somatostatinoma.

The HER2+ tumors treated by the present invention may be defined by grade, and may be low grade, medium grade, or high grade HER2+ tumors. In specific embodiments, the tumor is a functional HER2+ tumors. Alternatively, the HER2+ tumor is a non-functional HER2+ tumor.

In particularly preferred embodiments, the cancer to be treated, diagnosed and/or staged is a small cell lung cancer. In other preferred embodiments, the cancer is a progressive midgut HER2+ tumor. In some embodiments, the invention provides therapy for such HER2+ tumors that are not responsive to Trastuzumab (Roche), Sandostatin (Novartis) or Somatuline® (Ipsen). In other embodiments, the HER2+ tumor is non-responsive or has a low response to an inhibitor of the PD-1/PD-L 1 pathway.

The present invention therapeutics, namely, the integrin antagonist peptidomimetic, [177Lu] DOTAGA IAC, permits targeting of cancers (HER2+) at locations that are beyond the blood brain barrier. In this manner, metastases that may not be reached by prior treatments, may be addressed by the present method, including the therapeutic treatment and diagnostic agents, and the use of the compounds to provide the therapeutic treatments and diagnosis.

The methods of the present invention also may utilize the therapeutic compounds of the invention in conjunction with a diagnostic, including compounds containing $\alpha v\beta 3$ and $\alpha v\beta 5$ anti-integrin antagonist peptidomimetic, displaying a selective affinity for the HER2+ protein, vitronectin, fibronectin, tenascin, reelin, kindlin, talin or combination thereof for the diagnosis or prognosis of disorders using PET, SPECT and MRI or combinations by administering an effective amount of activity thereof to a subject, particularly for the diagnosis of diseases related to metastasis and angiogenesis such as breast cancer, lung cancer, ovarian cancer, gastric cancer, esophageal cancer, blood borne cancers, musculoskeletal tumors, melanoma, head and neck cancer, human glioma, cervical cancer, vascular restenosis, osteoporosis, rheumatoid arthritis. According to some embodiments, a diagnostic detection method may involve the use of a compound containing the $\alpha v\beta 3$ and $\alpha v\beta 5$ integrin antagonist peptidomimetic, displaying a selective affinity for the HER2+ protein, vitronectin, fibronectin, tenascin, reelin, kindlin, talin or combination thereof, and may comprise a pharmaceutical composition comprising a therapeutically effective amount of the $\alpha v\beta 3$ and $\alpha v\beta 5$ antagonist peptidomimetic compound, covalently linked by a spacer sequence, wherein the compound may be a linear artificial sequence, a chelator such as NODAGA, DOTAGA, DOTATATE, CHX-A and a pharmaceutically acceptable excipient for targeted radionuclide therapy (TRNT). The compound may also be a radiotracer for nuclear medicine, such as the Gallium-68 or Fluorine-18, Zirconium-68, Copper-64, or Technetium-99m, covalently bound to a spacer, chelator, directly to the peptidomimetic, to a nanoparticle or to more than one amino acid unit of the peptidomimetic. The diagnostic compound is then administered to the patient, and a scan is carried out using a suitable scanning technique, such as, for example, PET, SPECT and MRI or combinations thereof.

Methods of treatment, diagnosis and staging of a disorder comprising the administration to an individual suffering from such disorder of a therapeutically effective amount of the αvβ3 and αvβ5 integrin antagonist peptidomimetic for targeted radionuclide therapy (TRNT), combination therapy, neoadjuvant therapy or adjuvant therapy. Therapeutic compounds with a strong affinity for the HER2+ protein are overexpressed in breast, esophageal, gastric and ovarian cancers and HER2+ metastases to the brain or other organs. Such compounds are able to decrease or eliminate the proliferation of tumor cells and/or to modulate pathologic angiogenesis via TRNT. Compounds containing αvβ3 and αvβ5 anti-integrin antagonist peptidomimetic, displaying a selective affinity for the HER2+ protein, vitronectin, fibronectin, tenascin, reelin, kindlin, talin or combination thereof for the diagnosis or prognosis of disorders using PET, SPECT and MRI or combinations by administering an effective amount of activity thereof to a subject, particularly for the diagnosis of diseases related to metastasis and angiogenesis such as breast cancer, lung cancer, ovarian cancer, gastric cancer, esophageal cancer, blood borne cancers, musculoskeletal tumors, melanoma, head and neck cancer, human glioma, cervical cancer, vascular restenosis, osteoporosis, rheumatoid arthritis. The aforementioned compound demonstrates safety and efficacy in animal and human mammalian models.

Peptides according to the invention can be used in oncology and nuclear medicine application for the diagnosis and treatment of cancers.

According to preferred embodiments, the invention accordingly provides a method of treatment of a disorder comprising the administration to an individual suffering from such a disorder of a therapeutically effective amount of the αvβ3 and αvβ5 integrin antagonist peptidomimetic for TRNT.

Examples of specific disorders include pathologies that are related to angiogenesis and metastasis, such as breast cancer, ovarian cancer, lung cancer, gastric cancer, esophageal cancer, musculoskeletal tumors, melanoma, head and neck cancer, blood cancers, human glioma, cervical cancer, vascular restenosis, osteoporosis, rheumatoid arthritis.

Particularly, the compounds of the invention are able to decrease the proliferation of tumor cells and/or to modulate pathologic angiogenesis via TRNT.

Even more particularly, the compounds of the invention demonstrate a strong affinity of the HER2+ protein overexpressed in around 20% of all breast, esophageal, gastric and ovarian cancers.

The inventive method also may implement companion diagnostics, in association with the therapeutic compounds. Companion diagnostic compounds may also be used in the diagnosis or prognosis of disorders using PET, SPECT and MRI or combinations by administering an effective amount thereof to a subject, particularly for the diagnosis of diseases related to metastasis and angiogenesis such as breast cancer, lung cancer, ovarian cancer, gastric cancer, esophageal cancer, blood borne cancers, musculoskeletal tumors, melanoma, head and neck cancer, human glioma, cervical cancer, vascular restenosis, osteoporosis, rheumatoid arthritis.

DETAILED DESCRIPTION OF THE INVENTION

The present invention provides methods of inhibiting the growth of a HER2+ tumor, methods of inhibiting proliferation of HER2+ tumor cells, methods of treating or stabilizing a HER2+ cancer, methods of inhibiting HER2+ tumor metastases, methods of reducing tumorigenicity of HER2+ tumor cells and methods of reducing the frequency of cancer stem cells or tumor initiating cells in a HER2+ tumor. More specifically, the methods provided herein comprise administering a combination of Peptide Receptor Radionuclide with an immune-oncology therapy. In some embodiments, the TRNT may be a therapy using a radiolabeled SSA peptide (Somatostatin analogue peptide) with high affinity for somatostatin receptors (SSTR) that carries a radioactive isotope such as Lu-177 within its overall structure. In the present invention, the TRNT may be combined with standard of care; Trastuzumab and chemotherapy in the neoadjuvant setting but may be used with a PD-1 and/or PD-L 1/CDLA-4 or similar inhibitor.

Tumor Targeted Radionuclide Therapy (TRNT)

The method involves administering a pharmaceutical composition that cytotoxic radiation to cancer cells, and in particular to the HER2+ cells, while preferably minimizing the toxicity to surrounding healthy tissue. The method involves delivering a radioligand that is designed specially to treat HER2+ cancers. The method may involve targeting the HER2+ cancel with the radiopharmaceutical, in particular with the radioligand that comprises the anti-integrin peptidomimetic, the chelator and radionuclide (such as [177] Lutetium or [225]Actinium). The anti-integrin peptidomimetic targets the HER2+ proteins or characteristic cell feature and specifically determines the localization of the radiopharmaceutical and the radionuclide carried by the composition is delivered to effect treatment. The methods herein also involve conducting diagnostics of cancers, and in particular HER2+ cancers, through non-invasive imaging by detection of γ-rays using positron emission tomography (PET) or single-photon emission computerized tomography (SPECT), and/or as therapeutics for TRNT to deliver cancer cell killing radiation to the targeted tumor cells. A composition is administered to the patient, and the imaging carried out to determine the existence or prognosis of the cancer, or for use in staging.

This αvβ3 integrin antagonist peptidomimetic has high affinity for integrins on the surface of or in cancerous tumors and exquisitely targets the HER2+ protein which is overexpressed in breast cancer. Administering the radiolabeled peptidomimetic targets the HER2+ cancer in a patient or subject.

TRNT and/or a companion diagnostic for pre-targeting has not been utilized or approved by a regulatory agency for treatment of any of the ten types of breast cancer including HER2+.

TRNT has advantages over conventional cancer drugs, in particular the absence of collateral effects of chemotherapy or immunotherapy. Unlike external beam therapy, it is organ specific and not systemic and is not dose limiting. There is a reduction in renal excretion and/or hepatic degradation, leading to prolonged circulation times and less accumulation in healthy non-target tissues and site-αvoidance drug delivery, accumulation at pathological sites and site-specific drug delivery. without the side effects of chemotherapy. As well, TRNT results in a high therapeutic index and accumulation at the targeted sites. The compound enables the monitoring drug delivery, drug release and drug efficacy, validation and optimization of combination therapies and to the ability to pre-screen patients, enabling personalized medicine. The efficient targeting capacity and fast clearance offers a high potential for targeted radionuclide therapy (TRNT). The pharmacokinetic and pharmacodynamic properties match the decay properties of the short-lived alpha and beta particle emitting radionuclides, offering a treatment option for solid tumors, metastases, micrometastatic cancer and residual disease.

A preferred implementation of the method involves treating a patient that has a human epidermal growth factor receptor 2-Positive, hereinafter referred to as HER2+, or other cancer that overexpresses integrin receptors with a pharmaceutical composition that is administered to the patient. The method involves administering to the patient a combination of a pharmacologically effective amount of an antagonist peptide mimetic compound of an integrin whose molecular structure includes a tetrahydropyridimidinyl-aminoethyloxybenzoyl group on a sulfonylamino-β-alanine nucleus, exhibiting selective, high binding affinity for $\alpha5\beta3$, hereinafter referred to as β3 integrin receptor when further substituted on the sulfonyl moiety with an N-amino alkycarbamyl group or a butyloxycarbonylamino alkylcarbamoyl group or similar groups with a chelating agent, and a diagnostic or therapeutic radionuclide for tumor-targeted β3 peptide mimetic receptor radionuclide therapy (hereinafter referred to as TRNT).

According to a preferred embodiment, the therapeutic compound comprises Lu-177 DOTAGA IAC: A ligand containing the active moiety, the $\alpha V\beta3$ integrin antagonist peptidomimetic, 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) and 1-(1-carboxy-3-carbon tert butoxymethyl)-1,4,7,10-tetraazacyclododecane (DOTAGA) (tBu)4 to radiolabel with Lutetium-177 for peptide receptor Lutetium therapy. The method may provide the pharmaceutical in a kit form that may generate or comprise a ready-to-inject solution of the radioligand.

The invention involves administering the compound of the invention to treat certain HER2+'s by selectively binding to SSTR2 receptors, the most commonly expressed receptors on these types of tumors. The compound of the invention then destroys HER2+ cells in a targeted fashion by delivering a local emission of high-energy electrons. Because The compound of the invention also emits gamma radiation, it can also be useful as a disease management tool, as this kind of emission can be captured with a SPECT camera and thus be used for determining the drug's distribution and pharmacokinetics and also for dosimetric estimations.

In light of the current limited options and effectiveness for treatment of HER2+s overall and the lack of treatments for progressive midgut HER2+s specifically, the invention can meet a significant medical need by potentially improving patient outcomes in the treatment of progressive midgut HER2+s, as well as other somatostatin-receptor tumors.

The invention provides what the inventor considers is the first ever TRNT radiopharmaceutical product being tested in a Phase 1/2 trial for the treatment of inoperable, progressive, HER2+ cancers.

Methods of Treatment

The present invention provides methods of treating HER2+ tumors and include a group with a wide range of morphologic, functional, and behavioral characteristics. These tumors are generally slow growing but have the potential to spread, primarily to the liver or brain, and when they do, they can be life threatening and difficult to treat with current modalities.

HER2+ tumors have traditionally been classified by the site of their origin. In certain embodiments, the HER2+ is selected from the group consisting of pancreatic HER2+ tumors (pHER2+s) and tumors of the lung, stomach, duodenum, jejunum, ileum, colon and rectum. In further embodiments, the HER2+ is selected from the group consisting HER2+ tumors of the ovary, thymus, thyroid medulla, adrenal glands (e.g., pheochromocytoma) and paraganglia (paraganglioma). In certain embodiments, the HER2+ treated by the methods described herein is small cell lung cancer (SCLC). In certain alternative embodiments, the HER2+ is a non-small cell lung cancer. In certain embodiments, HER2+s are pancreatic HER2+ tumors (PETS) or carcinoid tumors. In certain embodiments, the HER2+ is non-small cell lung cancer, pancreatic cancer, or thyroid cancer.

HER2+ tumors are also classified by grade and differentiation. See, e.g., Phan et al., Pancreas, 39(6):784-798 (2012). In certain embodiments, the HER2+ tumor is a well differentiated, low grade tumor. In certain embodiments, the HER2+ tumor is a moderately differentiated, intermediate grade tumor. In certain embodiments, the HER2+ tumor is poorly differentiated, high grade tumor. In one embodiment, low grade tumors are characterized by <2 mitoses per 10 HPF (high power fields) and no necrosis. In one embodiment, intermediate grade tumors are characterized by 2-10 mitoses per 10 HPF (high power fields) or foci of necrosis. In one embodiment, high grade tumors are characterized by >10 mitoses per 10 HPF (high power fields).

In other embodiments HER2+ tumors can be divided based on the WHO classification 2000 and 2010 into HER2+ tumors Grade 1-Grade 2 (or Well-differentiated endocrine tumor or carcinoma (WDET/WDEC), HER2+ carcinoma Grade 3 or Poorly differentiated endocrine carcinoma/small-cell carcinoma (PDEC), Mixed adenoHER2+ carcinoma (MANEC) and Hyperplastic and preneoplastic lesions. According to the HER2+ SIWHO/AJCC Classification systems Tumors G1 are those with Ki67 index <2% or MI (mitotic count)<2, Tumors G2 are those with Ki67 index within 3-20% or MI=2-20 and tumors G3 are those with Ki67 index>20% or MI>20.

HER2+ tumors are also classified as functional and non-functional HER2+s. HER2+s are considered functional when a specific clinical syndrome is induced due to excessive production of hormones by the tumor cells. Examples of functional HER2+s include, but are not limited to, carcinoid tumors, which can result in carcinoid syndrome, and functional pHER2+s, for example, insulinomas, gastrinomas, vasoactive intestinal peptide (VIPomas), glucagonomas, and somatostatinomas.

Non-functional HER2+s are not associated with a clinical syndrome due to excessive production of hormones by the tumor cells, but can still produce symptoms related to the presence of the tumor or its metastasis (e.g., abdominal pain or bloating). In certain embodiments, the HER2+ tumor is a functional HER2+. In certain embodiments, the HER2+ tumor is a non-functional HER2+. In certain embodiments, the HER2+ tumor is selected from the group consisting of functional carcinoid tumor, insulinoma, gastrinoma, vaso active intestinal peptide VIPoma, glucagonoma, serotoninoma, histaminoma, ACTHoma, pheochromocytoma, and somatostatinoma. In certain embodiments, the HER2+ tumor is NSCLC.

In certain embodiments, the HER2+ tumor is a primary tumor. In alternative embodiments, the HER2+ tumor is metastatic tumor. In certain embodiments, the HER2+ tumor has not spread outside of the wall of the primary organ. In certain embodiments, the HER2+ tumor has spread through the wall of the primary organ and to nearby tissues, such as fat, muscle, or lymph nodes. In certain embodiments, the HER2+ tumor has spread to tissues or organs away from the primary organ, for example, to the liver, bones, or lungs.

In specific embodiments, it is contemplated that the methods of the present invention will be particularly useful in the treatment of HER2+ cancer or tumor that is refractory to treatment. As a non-limiting example, the cancer or tumor may be chemorefractory (i.e., resistant to one or more forms of chemotherapy). In certain embodiments, the cancer or tumor is resistant to treatment with a somatostatin analog. In certain embodiments, the cancer or tumor is resistant to treatment with a kinase inhibitor. In still other embodiments the cancer or tumor is resistant to treatment with an inhibitor of the PD-1/PD-L 1/CTLA-4 pathway.

In certain embodiments, the HER2+ cancer or tumor has metastasized to the liver. By way of non-limiting example, the HER2+ cancer or tumor is a carcinoid or pancreatic HER2+ tumor that has metastasized to the liver.

Compounds useful in connection with the invention may be produced by methods well known to those of skill in the art. Exemplary such methods include those described in U.S. Pat. Nos. 5,804,157 or 5,830,431, the complete disclosures of which are herein incorporated by reference.

The present invention provides for methods of treating HER2+ tumor comprising administering a therapeutically effective amount of a Tumor Targeted Radionuclide Therapy (TRNT) in combination with an inhibitor of the PD-1/PD-L 1/CTLA-4 pathway to a subject (e.g., a subject in need of treatment). In certain embodiments, the HER2+ tumor is a pancreatic HER2+ tumor. In certain embodiments, the HER2+ tumor is a carcinoid. In certain embodiments, the HER2+ tumor is HER2+ tumor of the lung. By way of non-limiting example, the HER2+ tumor in the lung may be SCLC. The invention is particularly useful for the treatment of HER2+ tumors that overexpress SSTR in their cellular surface such as (but not limited to) pituitary adenomas, gastrointestinal and pancreatic endocrine carcinomas (GEP-NET tumors), pulmonary HER2+, paragangliomas, pheochromocytomas, small cell lung cancers, medullary thyroid carcinomas, breast cancers, prostate cancer and malignant lymphomas. In certain embodiments, the subject is a human. In certain embodiments, the TRNT is the invention, for example, comprising the compositions and their application to deliver a therapeutically effective treatment to the patient.

The present invention further provides methods for inhibiting HER2+ tumor growth using a therapeutically effective amount of a TRNT in combination with an inhibitor of the PD-1/PD-L 1/CTLA-4 pathway to a subject. In certain embodiments, the method of inhibiting the HER2+ tumor growth comprises contacting the tumor cell with a therapeutically effective amount of one or both of a TRNT and with an inhibitor of the PD-1/PD-L 1/CTLA-4 pathway to a subject in vitro. For example, an immortalized HER2+ tumor cell line is cultured in medium to which is added the TRNT to inhibit tumor growth. In some embodiments, HER2+ tumor cells are isolated from a patient sample such as, for example, a tissue biopsy, pleural effusion, or blood sample and cultured in medium to which is added the TRNT and/or the inhibitor of the PD-1/PD-L 1/CTLA-4 pathway to inhibit tumor growth.

In some embodiments, the method of inhibiting HER2+ tumor growth comprises contacting the HER2+ tumor or tumor cells with combination therapy of the present invention in vivo. In certain embodiments, contacting a HER2+ tumor or tumor cell with a TRNT and an inhibitor of the PD-1/PD-L 1/CTLA-4 pathway is performed in an animal model. For example, a TRNT and an inhibitor of the PD-1/PD-L 1/CTLA-4 pathway may be administered to HER2+ tumor xenografts that have been grown in immunocompromised mice (e.g. NOD/SCID mice) to inhibit HER2+ tumor growth. In some embodiments, HER2+ tumor cancer stem cells are isolated from a patient sample such as, for example, a tissue biopsy, pleural effusion, or blood sample and injected into immunocompromised mice that are then administered the combination therapy of the present invention (i.e., a TRNT and an inhibitor of the PD-1/PD-L 1/CTLA-4 pathway) to inhibit HER2+ tumor cell growth. In some embodiments, the TRNT and/or the PD-1/PD-L 1/CTLA-4 pathway inhibitor is administered at the same time or shortly after the introduction of tumorigenic cells into the animal to prevent HER2+ tumor growth. In some embodiments, the TRNT and/or the inhibitor of the PD-1/PD-L 1/CTLA-4 pathway is administered as a therapeutic after the tumorigenic cells have grown to a specified size.

In certain embodiments, the method of inhibiting HER2+ tumor growth comprises administering to a subject a therapeutically effective amount of the TRNT and the inhibitor of the PD-1/PD-L 1/CTLA-4. In certain embodiments, the subject is a human. In certain embodiments, the subject has a HER2+ tumor or has had a tumor removed.

In certain embodiments, the HER2+ tumor is a pancreatic HER2+ tumor. In certain embodiments, the HER2+ tumor is a carcinoid. In certain embodiments, the HER2+ tumor is HER2+ tumor of the lung. In certain embodiments, the HER2+ tumor is NSCLC.

In addition, the invention provides a method of reducing the tumorigenicity of a HER2+ tumor in a subject, comprising administering a therapeutically effective amount of a TRNT and an inhibitor of the PD-1/PD-L1 to the subject. In certain embodiments, the HER2+ tumor comprises cancer stem cells. In certain embodiments, the frequency of cancer stem cells in the HER2+ tumor is reduced by administration of the agent. In certain embodiments, the TRNT is The invention.

Thus, the invention also provides a method of reducing the frequency of cancer stem cells in a HER2+ tumor, comprising contacting the tumor with an effective amount of a TRNT and an inhibitor of the PD-1/PD-L 1/CTLA-4 pathway.

As noted herein, the PORT is administered in combination with an inhibitor of the PD-1/PD-L 1 pathway. In such methods, the TRNT may be administered prior to, concurrently with, and/or subsequently to administration of the PD-1/PD-L 1/CTLA-4 inhibitor. Pharmaceutical compositions comprising the TRNT and the PD-1/PD-L 1/CTLA-4 inhibitor are also provided. It is contemplated that the combined treatment with the TRNT and the PD-1/PD-L 1/CTLA-4 inhibitor has a synergistic effect on the treatment of the HER2+s.

It will be appreciated that the combination of a TRNT and the PD-1/PD-L 1/CTLA-4 inhibitor agent may be administered in any order or concurrently. In selected embodiments, the TRNT and PD-1/PD-L 1/CTLA-4 will be administered to patients that have previously undergone treatment with other anti-cancer agents. In certain other embodiments, the TRNT and the PD-1/PD-L 1/CTLA-4 inhibitor agent will be administered substantially simultaneously or concurrently. For example, a subject may be given TRNT while undergoing a course of treatment with the PD-1/PD-L 1/CTLA-4 inhibitor agent. In addition it is contemplated that the subject has already or may be concurrently receiving other forms of cancer therapy, e.g., chemotherapy. In certain embodiments, the TRNT will be administered within 1 year of the treatment with the PD-1/PD-L 1/CTLA-4 inhibitor agent. In certain alternative embodiments, the TRNT will be administered within 10, 8, 6, 4, or 2 months of any treatment with the PD-1/PD-L 1/CTLA-4 inhibitor agent and/or additional anti-cancer agent. In certain other embodiments, the TRNT will be administered within 4, 3, 2, or 1 week of any treatment with the PD-1/PD-L 1/CTLA-4 inhibitor agent and/or additional anti-cancer agent. In some embodiments, the TRNT will be administered within 5, 4, 3, 2, or 1 days of any treatment with the PD-1/PD-L 1/CTLA-4 inhibitor agent and/or additional anti-cancer agent. It will further be appreciated that the TRNT and the PD-1/PD-L 1/CTLA-4 inhibitor agent and/or additional anti-cancer agent or treatment may be administered to the subject within a matter of hours or minutes (i.e., substantially simultaneously).

In addition to the administration of the combination of TRNT and at least one PD-1/PD-L 1 inhibitor, it may be useful to also administer additional anticancer agents. Useful classes of anti-cancer agents include, for example, anti-tubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, anti-metabolites, chemotherapy sensitizers, duocarmycins, etoposides, fluorinated pyrimidines, ionophores, lexitropsins, nitrosoureas, platinols, performing compounds, purine anti metabolites, puromycins, radiation sensitizers, steroids, taxanes, topoisomerase inhibitors, vinca alkaloids, or the like or may be attached to a nanoparticle which crossed the blood-brain barrier for delivery of this cytotoxic agent to brain tumors. In certain embodiments, the second anti-cancer agent is an antimetabolite, an antimitotic, a topoisomerase inhibitor, or angiogenesis inhibitor.

Anticancer agents that may be administered in combination with the TRNT and PD-1/PD-L 1/CTLA-4 inhibitor include chemotherapeutic agents. Thus, in some embodiments, the method or treatment involves the combined administration of a TRNT and PD-1/PD-L 1/CTLA-4 inhibitor and a chemotherapeutic agent or cocktail of multiple different chemotherapeutic agents. Treatment with a TRNT can occur prior to, concurrently with, or subsequent to administration of these other therapies. Chemotherapies contemplated by the invention include chemical substances or drugs which are known in the art and are commercially available, such as gemcitabine, irinotecan, doxorubicin, 5-fluorouracil, cytosine arabinoside ("Ara-C"), cyclophosphamide, thiotepa, busulfan, cytoxan, Taxol or taxene, methotrexate, cisplatin, melphalan, vinblastine and carboplatin. Combined administration can include co-administration, eitHER2+ in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner.

In certain embodiments, the treatment involves the combined administration of a PORT and PD-1/PD-L 1/CTLA-4 inhibitor described herein and radiation therapy. Treatment with the TRNT can occur prior to, concurrently with, or subsequent to administration of radiation therapy. Any dosing schedule for such radiation therapy can be used as determined by the skilled practitioner.

In some embodiments, the second anti-cancer agent comprises an antibody. Thus, treatment can involve the combined administration of a TRNT and the PD-1/PD-L 1/CTLA-4 inhibitor agent with antibodies against tumor-associated antigens including, but not limited to, antibodies that bind to EGFR, ErbB2, HER2+, DLL4, Notch and/or VEGF. In certain embodiments, the second anti-cancer agent is an antibody that is an angiogenesis inhibitor (e.g., an anti-VEGF antibody). In certain embodiments, the second anti-cancer agent is an inhibitor of Notch signaling. In certain embodiments, the second anti-cancer agent is Avastin (Bevacizumab), Trastuzumab (Trastuzumab), Vectibix (Panitumumab), or Erbitux (Cetuximab). Combined administration can include co-administration, either in a single pharmaceutical formulation or using separate formulations, or consecutive administration in either order but generally within a time period such that all active agents can exert their biological activities simultaneously.

Furthermore, treatment can include administration of one or more cytokines (e.g., lymphokines, interleukins, tumor necrosis factors, and/or growth factors) or can be accompanied by surgical removal of cancer cells or cytoreductive treatments such as (chemo-radio)embolization, radiofrequency ablation and high-intensity focused ultrasound (HIFU) ablation or any other therapy deemed necessary by the treating physician.

Preferably, TRNT with the therapeutic treatment using the compounds of the invention is given in a cycle wherein each cycle comprises 3.7-7.4 GBq administered intravenously. Typically, a therapeutic cumulative activity (dose) of approximately 30 GBq may readily be divided into 4 to 6 cycles, each administered every 5 to 12 weeks. It should be understood that longer intercycle intervals as long as κ Months or even years can be used. Moreover, the patient may be treated with multiple rounds of the 4 to 6 cycles after months or years from the first set of treatments. The second and subsequent set of treatments may use the same activities (doses) or may use different activities (doses) depending on the experience of the center and of the characteristics and therapeutic needs of each patient.

Anti-PD-1 nivolumab is typically administered intravenously at doses of about 3 mg/kg every 2-3 weeks, for an initial period of two years. Thereafter, maintenance therapy every 12 weeks after the initial treatment are frequently used. It should be understood that these dosing regimens will vary according to the patient's response to the treatments and at the discretion of the treating clinician. The recommended dose of ipilimumab for the treatment of unresectable or metastatic melanoma is 3 mg/kg administered intravenously over 90 minutes every 3 weeks for a total of four doses.

The TRNT and the PD-1/PD-L 1/CTLA-4 inhibitors (e.g., antibodies and soluble receptors) can be formulated into a pharmaceutical composition by any suitable method known in the art. In certain embodiments, the pharmaceutical compositions comprise a pharmaceutically acceptable vehicle. The pharmaceutical compositions find use in inhibiting HER2+ tumor growth and treating HER2+ tumor in human patients.

The methods and therapeutic compositions of the present invention may be used in connection with a diagnostic. The diagnostic may be administered to the patient to identify areas of tumor or cancer cells or growth, and may be used to determine one or more subsequent treatment parameters for a treatment protocol, such as the treatment dosage and extent (e.g., where the treatment involves administering an a treatment compound according to the invention, such as the preferred composition, the integrin peptidomimetic Lu-177 DOTAGA IAC construct. According to some embodiments, a preferred diagnostic composition may comprise Ga-68-NODAGA IAC: A ligand containing the active moiety, the αVβ3 integrin antagonist peptidomimetic 4-[2-(3,4,5,6-tetrahydropyrimidine-2-ylamino)ethyloxy]benzoyl-2-[N-(3-aminoneopenta-1-carbamyl)]-aminoethylsulfonyl-amino-β-alanine (IAC) and to 1-(1-carboxy-3-carbo-t-butoxypropyl)-4,7-(carbo-tert-butoxymethyl)-1,4,7-triazacyclononane.

The diagnostic and the therapeutic compositions preferably are prepared from components of a kit, where the composition is prepared and radiolabeled with the respective radionuclide prior to administering the composition to a patient/subject, which preferably is done intravenously.

PROPOSED EXAMPLES

Proposed Example 1

Example 1: a preferred compound of the invention, comprising Lu-177 DOTAGA IAC, is administered to a human patient at a fixed dose of 7.4 GBq (every 12 weeks) up to a cumulative dose which is tolerated by the patient (maximum 29.6 GBq). The preferred compound preferably is administered intravenously. Nivolumab is administered twice for each treatment of the preferred Lu-177 DOTAGA IAC compound, at a dose of 3 mg/Kg: one administration seven days before (d-7) and the other administration seven days after (d-positive7) administration of the compound of the invention, with the aim of achieving an effective PD-1/PD-L1 blockade, but also in the need not to overlap the anticipated lymphocyte nadir related to the lymphocytopenia-induced effect of the compound of the invention.

Studies have shown that intravenous administration of amino acids has a renal protective effect. An infusion of amino acids (containing lysine and arginine) could be done 30 to 45 minutes before the administration of 177Lu-DOTATATE and last for 3 to 4 hours.

Proposed Example 2

Example 2: In a proposed example, the compound of the present invention was administered to a patient suffering from HER2+breast cancer. The patient was given the compound of the invention (e.g., in an amount of from about 3.7-7.4 GBq) administered intravenously, and representing a dosage. One or more, and preferably a plurality of subsequent treatments of a similar amount are dosed to the patient intravenously, a couple to a few weeks from the first dosage. In this example, an additional therapeutic may be administered on either side of a window based on when the patient receives the inventive compound doses, e.g., such as seven days prior to a dose and seven days after a dose.

Proposed Example 3

Example 3: The patient was treated as in proposed example 1, above, however, prior to treatment with the Lu-177 DOTAGA IAC, the patient was diagnosed using the preferred diagnostic composition, comprising Ga-68-NODAGA IAC.

Proposed Example 4

Example 4: The patient was treated as in proposed example 2, above, however, prior to treatment with the Lu-177 DOTAGA IAC, the patient was diagnosed using the preferred diagnostic composition, comprising Ga-68-NODAGA IAC.

Proposed Example 5

Example 5: The patient was treated as in Example 1, but with the radionuclide consisting of one or more of: Actinium-225, Bismuth-213, Thorium-227, Lead-212, Astatine-211, Yttrium-90, Iodine-131, Gallium-68, and Zirconium-68.

Proposed Example 6

Example 6: The patient was treated as in Example 5, but with the chelator comprising one or more of: 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC), and (ii) at least one of the following:
  (a) 1-(1-carboxy-3-carbotertbutoxymethyl)-1,4,7,10-tetraazacyclododecane (DOTAGA) (tBu)$_4$; or
  (b) 4-[4,7-Bis-(carboxymethyl)-[1,4,7]triazonan-1-yl]-4-carboxy-butyryl (NODAGA); or
  (c) DOTATATE; or
  (d) C26H34N4O10S (CHX-A).

Breast cancer metastasis to the brain develops after a clinical latency of years to even decades, suggesting that colonization of the brain is the most challenging step of the metastatic cascade. However, the underlying mechanisms used by breast cancer cells to successfully colonize the brain's microenvironment remain elusive. Reelin is an archetypal extracellular glycoprotein that regulates migration, proliferation, and lamination of neurons. It is epigenetically silenced in various cancers, and its expression in multiple myelomas is linked to poor patient survival. Reelin expression was low in primary breast cancer tissue. However, its expression is significantly higher in HER2+breast cancers metastasizing to the brain. In particular, Reelin was highly expressed in the tumor periphery adjacent to surrounding astrocytes. This augmented Reelin expression was seen in HER2+ metastases, but not in triple negative (TN) primary tumors or in TN breast to brain metastasis cells co-cultured with astrocytes. The relative growth and rate of spheroids formation derived from HER2+ primary and BBM cells co-cultured with astrocytes were higher than those of TN primary and BBM cells, and knockdown of both Reelin and HER2+ suppressed the astrocyte-induced growth and spheroid forming ability of HER2+ cells. Within the neural niche, astrocytes epigenetically regulate Reelin expression and its interaction with HER2+ leading to increased proliferation and survival fitness.

Kindlin

Kindlins are a small family of 4.1-ezrin-radixin-moesin (FERM)-containing cytoplasmic proteins. Kindlin-3 is expressed in platelets, hematopoietic cells, and endothelial cells. Kindlin-3 promotes integrin activation, clustering and outside-in signaling. Aberrant expression of kindlin-3 was reported in HER2+breast cancer. Intriguingly, kindlin-3 positively regulates cancer cell metastasis. The expression of kindlin-3 in HER2+ cancer cells and its role in metastasis has been reported. This data demonstrates that despite its well-established role as a positive regulator of integrin-mediated cell adhesion, aberrant expression of kindlin-3 could lead to imbalanced Rho GTPases signaling that promotes cell migration. Kindlin-2 has been reported to be considered a key protein that couples cell adhesion by activating integrins and the induction of membrane protrusions by activating Rac1 and supplying Rac1 with the Arp2/3 complex. It has been reported that Kindlin 2 markedly downregulates the expression of miR-200 family by inducing CpG island hypermethylation. Mechanistically, Kindlin 2 forms a complex with DNMT3A in the cell nucleus and the two proteins co-occupy the promoter of miRNA-200b. Functionally, repression of miR-200b is required for Kindlin 2-induced breast cancer cell invasion and tumor formation. Kindlin 2 plays a novel role in epigenetic repression of miR-200 family, a mechanism that promotes breast cancer invasion. miR-200b is required for Kindlin 2-induced breast cancer cell invasion and tumor formation. data suggest a novel mechanism that Kindlin-2 regulates breast cancer progression by inducing genome instability. Kindlin 2 plays a novel role in epigenetic repression of miR-200 family, a mechanism that promotes breast cancer invasion.

The alpha (5) beta (3) integrin antagonist targets several proteins or any combination thereof including integrins, vitronectin, fibronectin and tenascin. The one or more proteins and mRNAs that also may be targeted can include, but are not limited to Actin, Reelin, Talin, and Kindlin or any combination thereof and can be used as specific biomarkers and targeted in HER2+ positive cancers with a radiolabeled ligand.

The anti-integrin antagonist that is the subject of this invention adheres to the HER2+ protein and for some patients may be used in combination with standard of care or alone. This can be a 'break-through' in treatment and for some, enable targeting of brain metastases, micrometastases or recurrence.

The action of the HER2+ protein may be blocked using the alpha5 beta 3 integrin antagonist peptidomimetic that attaches to specific proteins and disrupts its function.

TRNT might improve survival rates for women with stage 2 to 4 HER2+breast cancer significantly.

The HER2+ protein is expressed at high levels in several other cancers besides breast cancer. The radioligand enables treatment of some patients with HER2+ gastric, gastroesophageal junction, ovarian or HER2+ cancer that has metastasized to other organs including brain. This radioligand works by blocking HER2+ from sending signals to other proteins that cause cells to grow and replicate and destroying the cancer cells with radiation or impairing the DNA so the cells cannot replicate.

This $\alpha v \beta 3$ integrin antagonist peptidomimetic has high affinity for integrins on the surface of or in cancerous tumors and exquisitely targets the HER2+ protein which is overexpressed in breast cancer. Serendipitously, it was discovered that in addition to adhering to integrins, tenascin, vitronectin and fibronectin, that reelin, actin, talin and kindlin are also targeted. These are important targets in tumor and micrometastatic targeting. Potentially, ovarian, gastric. gastroesophageal junction, brain metastases and other HER2+ cancers can be treated.

Reelin, an archetypal extracellular glycoprotein highly expressed in the tumor in HER2+breast cancer tumors, enabling precise delivery of the radioligand consisting of an anti-integrin peptidomimetic, a chelator and a radionuclide which may be Lutetium-177 or Actinium-225 that can destroy cancerous cells, including micrometastases. Astrocyte induced reelin expression drives proliferation of HER2+breast cancer metastases. By measuring reelin expression in breast cancer-derived cell lines before and after TRNT treatment, it has been established that reelin plays an important role in invasiveness and metastatic potential of breast cancer cells and has an important role in invasiveness and metastases. Breast cancer metastasis to the brain develops after a clinical latency of years to even decades, suggesting that colonization of the brain is the most challenging step of the metastatic cascade. However, the underlying mechanisms used by breast cancer cells to successfully colonize the brain's microenvironment remain elusive. Reelin is an archetypal extracellular glycoprotein that regulates migration, proliferation, and lamination of neurons. It is epigenetically silenced in various cancers, and its expression in multiple myelomas is linked to poor patient survival. Reelin is a secreted, signaling protein associated with neuronal cell positioning and migration. It has been reported that reelin was found to be epigenetically silenced in gastric and pancreatic cancers in which down-regulation was associated with increased migratory ability and reduced survival. Reelin expression was analyzed by immunohistochemistry in 17 normal breast tissue samples from reduction mammoplasties and in two independent tissue microarrays of 136 and more than 2000 breast cancer biopsy samples, respectively. Results were analyzed with regard to clinical parameters, including BRE (Bloom, Richardson, Elston) grade, nodal status, estrogen receptor and HER2+ status, and overall survival. Reelin was expressed in the luminal epithelium and myoepithelium of the normal human breast but not in cancerous breasts. Loss of reelin protein expression correlated significantly with decreased survival (P=0.01) and positive lymph node status (P<0.001). By measuring reelin expression and promoter methylation status in 39 primary breast tumors, as well as in breast cancer-derived cell lines before and after decitabine treatment, Reelin expression levels correlated inversely with promoter methylation status, whereas demethylation increased reelin mRNA expression in vitro. Reelin overexpression in MDA-MB231 cells, as well as incubation with recombinant reelin, suppressed cell migration, invadopodia formation, and invasiveness in vitro. A syngeneic mouse mammary tumor transplantation model was used to examine the impact of host-derived reelin on breast cancer progression. It was found that transplanted syngeneic tumors grew more slowly in reelin-deficient ($rl^{Orl-/-}$) mice and had delayed metastatic colonization of the lungs. Immunohistochemistry of primary tumors revealed that tumors grown in $rl^{Orl-/-}$ animals had fewer blood vessels and increased macrophage infiltration. Gene expression studies from tumor tissues indicate that loss of host-derived reelin alters the balance of M1- and M2-associated macrophage markers, suggesting that reelin may influence the polarization of these cells. Consistent with this, $rl^{Orl-/-}$ M1-polarized bone marrow-derived macrophages have heightened levels of the M1-associated cytokines iNOS and IL-6. Based on these observations, there has been proposed a novel function for the reelin protein in breast cancer progression. It has been concluded that that reelin may play an important role in controlling invasiveness and metastatic potential of breast cancer cells and that its expression is controlled by promoter methylation. Reelin expression has been found to be low in primary breast cancer tissue. However, its expression was significantly higher in HER2+breast cancers metastasizing to the brain. In particular, Reelin was highly expressed in the tumor periphery adjacent to surrounding astrocytes. This augmented Reelin expression was seen in HER2+ metastases, but not in triple negative (TN) primary tumors or in TN breast to brain metastasis cells co-cultured with astrocytes. Furthermore, the elevated expression was sustained in HER2+ cells grown in the presence of the DNA methyltransferase inhibitor 5-azacytidine, indicating epigenetic regulation of Reelin expression. The relative growth and rate of spheroids formation derived from HER2+ primary and BBM cells co-cultured with astrocytes were higher than those of TN primary and BBM cells, and knockdown of both Reelin and HER2+ suppressed the astrocyte-induced growth and spheroid forming ability of HER2+ cells. Within the neural niche, astrocytes epigenetically regulate Reelin expression and its interaction with HER2+ leading to increased proliferation and survival fitness. Reelin/integrin cell adhesion underscores the therapeutic potential of targeting reelin/integrin expression in HER2+ tumors.

What is claimed is:

1. A method of treating a patient that has a human epidermal growth factor receptor 2 positive (HER2+) breast cancer, the method comprising administering to said patient a composition comprising 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) conjugated to 1-(1-carboxy-3-carbotertbutoxymethyl)-1,4,7,10-tetraazacyclododecane (DOTAGA)(tBu)$_4$) and radiolabeled with $^{177}$Lu in combination with a PD-1, PD-L1, or CTLA-4 inhibitor, wherein the inhibitor is selected from the group consisting of one or more of: Nivolumab, MK-3475, MPDL3280A, MED14736, ipilimumab, and tremelimumab.

2. A method of treating a patient that has a human epidermal growth factor receptor 2 positive (HER2+) breast cancer, the method comprising administering to said patient a composition comprising 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) conjugated to 1-(1-carboxy-3-carbotertbutoxymethyl)-1,4,7,10-tetraazacyclododecane (DOTAGA)(tBu)$_4$) and radiolabeled with an alpha emitter $^{225}$Ac in combination with a PD-1, PD-L1, or CTLA-4 inhibitor, wherein the inhibitor is selected from the group consisting of one or more of: Nivolumab, MK-3475, MPDL3280A, MED14736, ipilimumab, and tremelimumab.

3. The method of claim 1, wherein treating the patient that has the human epidermal growth factor receptor 2 positive (HER2+) breast cancer, further comprises administering to said patient a composition comprising 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) conjugated to 1-(1-carboxy-3-carbotertbutoxymethyl)-1,4,7,10-tetraazacyclododecane (DOTAGA)(tBu)$_4$) and radiolabeled with $^{225}$Ac.

4. The method of claim 1, further comprising administering to the patient a companion diagnostic comprising: 4-[2-(3,4,5,6-tetrahydropyrimidine-2-ylamino)ethyloxy]benzoyl-2-[N-(3-aminoneopenta-1-carbamyl)]-aminoethylsulfonyl-amino-β-alanine (IAC) and conjugated to 1-(1-carboxy-3-carbo-t-butoxypropyl)-4,7-(carbo-tert-butoxymethyl)-1,4,7-triazacyclononane, radiolabeled with $^{68}$Ga, allowing sufficient time for said companion diagnostic to reach the target, imaging the patient by administering the companion diagnostic and scanning the patient using one or more of PET, SPECT and MRI, and using a designated imaging technique to obtain data.

5. The method of claim 2, further comprising administering to the patient a companion diagnostic comprising: 4-[2-(3,4,5,6-tetrahydropyrimidine-2-ylamino)ethyloxy]benzoyl-2-[N-(3-aminoneopenta-1-carbamyl)]-aminoethylsulfonyl-amino-β-alanine (IAC) and conjugated to 1-(1-carboxy-3-carbo-t-butoxypropyl)-4,7-(carbo-tert-butoxymethyl)-1,4,7-triazacyclononane, radiolabeled with $^{68}$Ga, allowing sufficient time for said companion diagnostic to reach the target, imaging the patient by administering the companion diagnostic and scanning the patient using one or more of PET, SPECT and MRI, and using a designated imaging technique to obtain data.

6. The method of claim 4, further comprising imaging the patient by administering the companion diagnostic and scanning the patient using one or more of PET, SPECT and MRI, and determining the effectiveness of the administered treatment with the $^{177}$Lu radiolabeled composition comprising 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) conjugated to 1-(1-carboxy-3-carbotertbutoxymethyl)-1,4,7,10-tetraazacyclododecane (DOTAGA)(tBu)$_4$) by obtaining data, wherein said data is obtained by administering the companion diagnostic prior to and after administration of the administered treatment, and determining whether the treatment is effective by comparing the data obtained by scanning with historical data of the location and density and identifying a reduction of the density at said location.

7. The method of claim 5, further comprising imaging the patient by administering the companion diagnostic and scanning the patient using one or more of PET, SPECT and MRI, and determining the effectiveness of the administered treatment with the $^{225}$Ac radiolabeled composition comprising 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) conjugated to 1-(1-carboxy-3-carbotertbutoxymethyl)-1,4,7,10-tetraazacyclododecane (DOTAGA)(tBu)$_4$) by obtaining data, wherein said data is obtained by administering the companion diagnostic prior to and after administration of the administered treatment, and determining whether the treatment is effective by comparing the data obtained by scanning with historical data of the location and density and identifying a reduction of the density at said location.

8. The method of claim 3, further comprising imaging the patient by administering the companion diagnostic and scanning the patient using one or more of PET, SPECT and MRI, and determining the effectiveness of the administered treatment with the $^{177}$Lu radiolabeled composition comprising 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) conjugated to 1-(1-carboxy-3-carbotertbutoxymethyl)-1,4,7,10-tetraazacyclododecane (DOTAGA)(tBu)$_4$) and with the $^{225}$Ac radiolabeled composition comprising 4-[2-(3,4,5,6-tetrahydropyrimidine-2-ylamino) ethyloxy]benzoyl-2-[N-(3-aminoneopenta-1-carbamyl)]-aminoethylsulfonyl-amino-β-alanine (IAC) conjugated to 1-(1-carboxy-3-carbotertbutoxymethyl)-1,4,7,10-tetraazacyclododecane (DOTAGA)(tBu)$_4$), by obtaining data, wherein said data is obtained by administering the companion diagnostic prior to and after administration of the administered treatment, and determining whether the treatment is effective by comparing the data obtained by scanning with historical data of the location and density and identifying a reduction of the density at said location.

9. The method of claim 8, wherein the companion diagnostic comprises: 4-[2-(3,4,5,6-tetrahydropyrimidine-2-ylamino)ethyloxy]benzoyl-2-[N-(3-aminoneopenta-1-carbamyl)]-aminoethylsulfonyl-amino-β-alanine (IAC) conjugated to 1-(1-carboxy-3-carbo-t-butoxypropyl)-4,7-(carbo-tert-butoxymethyl)-1,4,7-triazacyclononane, radiolabeled with $^{68}$Ga, and wherein administering said companion diagnostic includes allowing sufficient time for said companion diagnostic to reach the target, and imaging the patient by administering the companion diagnostic and scanning the patient using one or more of PET, SPECT and MRI, and using a designated imaging technique to obtain data.

10. The method of claim 2, wherein the composition radiolabeled with the alpha emitter $^{225}$Ac is a linear peptidomimetic.

\* \* \* \* \*